(12) United States Patent
Forssmann

(10) Patent No.: US 10,973,886 B2
(45) Date of Patent: Apr. 13, 2021

(54) USE OF A PHARMACEUTICAL COMPOSITION CONTAINING AT LEAST ONE DIGESTIVE ENZYME IN ARTIFICIAL FEEDING

(71) Applicant: Nordmark Arzneimittel GmbH & Co. KG, Uetersen (DE)

(72) Inventor: Kristin Forssmann, Heidgraben (DE)

(73) Assignee: Nordmark Arzneimittel GmbH & Co. KG, Uetersen (DE)

( * ) Notice: Subject to any disclaimer, the term of this patent is extended or adjusted under 35 U.S.C. 154(b) by 54 days.

(21) Appl. No.: 15/757,410

(22) PCT Filed: Aug. 31, 2016

(86) PCT No.: PCT/EP2016/070516
§ 371 (c)(1),
(2) Date: Mar. 5, 2018

(87) PCT Pub. No.: WO2017/037114
PCT Pub. Date: Mar. 9, 2017

(65) Prior Publication Data
US 2018/0236040 A1 Aug. 23, 2018

(30) Foreign Application Priority Data

Sep. 4, 2015 (DE) .................... 10 2015 114 859.5

(51) Int. Cl.
*A61K 38/46* (2006.01)
*A23L 33/195* (2016.01)
*A23L 33/00* (2016.01)
*A61K 9/00* (2006.01)
*A61K 9/10* (2006.01)
*A61K 9/08* (2006.01)
*A61K 38/16* (2006.01)
*A61K 47/18* (2017.01)

(52) U.S. Cl.
CPC .......... *A61K 38/465* (2013.01); *A23L 33/195* (2016.08); *A23L 33/40* (2016.08); *A61K 9/0053* (2013.01); *A61K 38/164* (2013.01); *C12Y 301/01003* (2013.01); *A23V 2002/00* (2013.01); *A61K 9/08* (2013.01); *A61K 9/10* (2013.01); *A61K 47/183* (2013.01)

(58) Field of Classification Search
CPC ...... A61K 38/465; A61K 9/0053; A61K 9/08; A61K 9/10; A23L 33/40; A23L 33/195; C12Y 301/01003; A23V 2002/00
See application file for complete search history.

(56) References Cited

U.S. PATENT DOCUMENTS

| 4,602,910 A | * | 7/1986 | Larkin | ............... A61J 1/2093 604/410 |
| 5,098,378 A | * | 3/1992 | Piontek | ............ A61J 15/0015 604/500 |
| 5,527,280 A | | 6/1996 | Goelz | |
| 2006/0121017 A1 | | 6/2006 | Margolin et al. | |
| 2010/0239559 A1 | | 9/2010 | Freedman et al. | |
| 2014/0276632 A1 | | 9/2014 | Pironti et al. | |

FOREIGN PATENT DOCUMENTS

| DE | 102 43 208 B4 | 4/2004 | |
| DE | 10 2009 006 594 A1 | 8/2010 | |
| DE | 102009006594 A1 * | 8/2010 | ........... A61K 9/0095 |
| UA | 000000010025 U | 10/2005 | |
| WO | 2006/044529 A1 | 4/2006 | |

OTHER PUBLICATIONS

Ferrie et al., Nutr. Clin. Pract., 2011, vol. 26, p. 349-351.*
Suzuki et al., Gasteroenterology, 1999, vol. 116, No. 2, p. 431-437.*
Blumenstein et al., World J Gastroenterol, Jul. 2014, vol. 20, No. 26, p. 8505-8524.*
Margaret Rosenfeld, et al., "Nutritional effects of long-term gastrostomy feedings in children with cystic fibrosis," Journal of the American Dietetic Association, vol. 99, No. 2, Feb. 1999, pp. 191-194.
Suzie Ferrie, et al., Pancreatic Enzyme Supplementation for Patients Receiving Enteral Feeds, Nutrition in Clinical Practice, vol. 26, no. 3, XP009178443, Jun. 2011, pp. 349-351.

(Continued)

*Primary Examiner* — Kade Ariani
(74) *Attorney, Agent, or Firm* — Oblon, McClelland, Maier & Neustadt, L.L.P.

(57) ABSTRACT

The invention relates to the use of a pharmaceutical composition in combination with a tube food provided for artificial feeding in the treatment of digestive disorders in case of artificial feeding, where the pharmaceutical composition contains or consists of at least one digestive enzyme, preferably a lipase, particularly preferably a bacterial lipase, most preferably burlulipase (INN) in liquid dosage form, wherein the pharmaceutical composition and the tube food are formulated for being administered simultaneously but separately from each other. The pharmaceutical composition can therefore be administered simultaneously and continuously during the administration of the tube food, but separately from it. As a result, the digestive performance of a patient being artificially fed can be enhanced significantly.

14 Claims, 4 Drawing Sheets

(56) References Cited

OTHER PUBLICATIONS

James E. Heubi, et al, "Safety and Efficacy of a Novel Microbial Lipase in Patients with Exocrine Pancreatic Insufficiency due to Cystic Fibrosis: A Randomized Controlled Clinical Trial," The Journal of Pediatrics, vol. 176, XP029705650, Sep. 2016, pp. 156-161.e1.

International Search Report dated Nov. 7, 2016 in PCT/EP2016/070516 filed Aug. 31, 2016.

German Search Report dated Feb. 24, 2016 in DE 102015114859.5 filed Sep. 4, 2015.

* cited by examiner

USE OF A PHARMACEUTICAL COMPOSITION CONTAINING AT LEAST ONE DIGESTIVE ENZYME IN ARTIFICIAL FEEDING

The invention relates to the use of a pharmaceutical composition containing at least one digestive enzyme in artificial nutrition.

If a patient is unable to ingest the necessary nutrition by oral administration, he must be artificially fed. Natural food intake via the mouth can be hindered or limited in a variety of diseases. For example, these are severe traumas, surgery and unconsciousness. In addition, artificial feeding is required in case of functional disorders of the digestive tract, for example, massive chewing and swallowing problems after a stroke, facial fractures or cervical tumors, or in case of diseases of the digestive organs such as stenoses of the intestine, mucoviscidosis, pancreatitis or Crohn's disease. Further indications include cachexia (severe emaciation) in case of cancer, immunological or chronic diseases. Also for some patients with senile dementia, Parkinson's disease or anorexia nervosa, it may be necessary to supply the food artificially.

The artificial feeding can be carried out via the digestive tract (enteral feeding), i.e. via a tube. Since in enteral feeding the food is supplied to the gastrointestinal tract via a tube, this is only possible if the digestive tract is still functioning. The choice of the tube depends on the estimated duration of feeding, the type of disease and the condition of the patient. Basically, there are several options for tube feeding If it takes presumably less than four weeks before the patient can eat again by himself, usually a tube is reasonable which is introduced through the nose. Depending on where it ends, the tube is called a gastric tube (gastric or nasogastric tube), a nasointestinal tube (the tube ends up in the intestine, such as duodenum or jejunum), a nasoduodenal tube (the probe ends in the duodenum) or a nasojejunal tube (the tube ends in the jejunum).

The tube in these cases is a thin hose that passes through the nose or mouth, throat and esophagus into the stomach or into part of the small intestine. The use of a tube requires unhindered passage in the nose and throat. In the case of tubes that end in the stomach, gastric emptying must also work. This form of feeding uses the entire digestive tract and thus corresponds to the normal feeding. The food is transferred in portions from the stomach to the intestine, and the gastrointestinal hormone production is activated in this way. An alternative to the nasogastric tube, for example, when the gastric emptying is disturbed, is the so-called nasojejunal tube, wherein the tube is passed into the small intestine. It passes via the nose through the stomach into a specific section of the small intestine, the jejunum. This tube is usually inserted using an endoscope. As this tube is thinner than a nasogastric tube, it disturbs the patient less and can therefore usually stay for a longer time. Nasojejunal tube feeding is usually continuous, as the jejunum does not have a storage function like the stomach has, making it less tolerable for larger portions of food.

If enteral nutrition is expected to be maintained for more than three weeks, it may be reasonable to place a percutaneous tube through the abdominal wall into the stomach, a so-called PEG probe (PEG: percutaneous endoscopic gastrostomy). Under local anesthesia as part of a gastroscopy, a thin plastic hose is passed through the abdominal wall into the stomach and is secured against slipping. In some cases, the tube is also placed in the adjacent small intestine, a so-called. PEJ tube (PEJ: percutaneous endoscopic jejunostomy). The procedure lasts a few minutes, is largely painless and also allows additional eating and drinking, as well as training of swallowing and eating.

The administration of the tube food is carried out similar to an infusion, by gravity or by an electronically controlled pump, usually continuously, less often in portions as a so-called "bolus dose". To avoid vomiting, the patient is in a sitting position or the upper body is rested in an elevated position. Preferably, the application of the food substrates is carried out by means of a feeding pump, in which the dropping speed can be set exactly and thus the desired amount of substrate can be accurately supplied. An inaccurate and irregular supply may lead to gastrointestinal intolerance in the affected person. The feed rate of the food substrate is, for example, 120 ml/h-150 ml/h.

Each person has their own individual need for food and liquid, which depends on various factors, such as age, height and weight, state of health, etc. Considering all aspects, the treating physician decides on the type and amount of the tube food to be administered and the hydration. Before starting an artificial feeding, therefore, the nutritional status of the patient is first determined in order to be able to dose the energy and nutrient supply in a suitable manner. To estimate the required energy supply, for example, the resting energy consumption is calculated on the basis of body size, weight, age and gender; in adults, this is usually about 20 to 24 kcal per kg of body weight per day.

The tube food is a nutrient solution which contains the necessary nutrients in a balanced composition. The nutrient solutions contain the necessary proteins, carbohydrates, fats, vitamins, minerals and trace elements. Medications can also be administered with/in the nutrient solution. In addition, liquid in the form of water or tea can be given through the tube.

PRIOR ART

There is a variety of tube food available: for example the tube food prepared in hospital kitchens or dietary kitchens, nutrient-defined or high molecular diets as well as chemically defined or low molecular diets, including special forms that are tailored to specific diseases. Industrially or synthetically produced products are always preferable to self-prepared food, as they are hygienically safer and provide a long-term supply of all nutrients. In addition, not all foods can be made suitable for supply by tubes. Also, an incorrect dosage of nutrients in the nutrient solutions can lead to complications. In addition, industrially manufactured products are "balanced", i.e. they are tailored to the nutritional needs.

The synthetically produced nutrient-defined or high molecular diets contain all nutrients—as in a conventional diet—in high molecular form: the proteins contained are, for example, the usual intact proteins, fats are long-chain triglycerides and carbohydrates are poly-, oligo- or monosaccharides. The polymers first have to be broken down enzymatically before they can be absorbed in the intestine, so that an intact digestive capacity is necessary for this tube food. The nutrient solutions are regularly adjusted to supply between 1 and 1.5 kcal per ml and are available with and without fibers.

For patients with limited digestive capacity, chemically defined or low molecular diets are suitable, which contain the nutrients in the form of rapidly digestible monomers, such as monosaccharides and individual amino acids, which can be absorbed in the small intestine without enzymatic splitting. Thus, for example, products with medium-chain triglycerides can be used in case of a fat digestion disorder. For short bowel syndrome and malabsorption or for immobilization of posterior intestinal sections, fiber-free diets with short-chain peptides are recommendable.

Tube food for patients is available in glass bottles or plastic bags. These are connected directly to the tube with a special hose. Bedridden patients usually receive their daily ration continuously, with a break of about six hours during the night. An electronic pump can control the feed rate. Mobile patients can also take up the food in portions, similar to the usual eating rhythm. For example, a daily ration of 1500 to 2000 ml contains all the necessary nutrients, vitamins and minerals. Only liquid has to be supplemented.

Tube feeding is known from prior art and numerous applications are described:

The Ukrainian utility model UA 10025 U refers to a method for preventing early postoperative gastrointestinal bleeding in patients fed enterally. Here, the acid production in the stomach is decreased by administering an acidin-pepsin solution into the small intestine throughout the period of the artificial feeding. Pepsin is a digestive enzyme, a so-called peptidase, which is produced in the stomach of vertebrates and thus also of humans. It is a phosphoprotein with 327 amino acids. Acidin is a betaine hydrochloride; this is an oxidation product of choline and a derivative of the amino acid glycine. Commercially available pepsin most often comes from the stomach of pigs and thus has the disadvantages of animal products, such as risks of contamination and problems of tolerability. The use of a lipase is not mentioned here.

Further, DE 10 2009 006 594 A1 discloses pharmaceutical preparations for the treatment of pancreatic insufficiency, e.g. mucoviscidosis or other pancreatic diseases. A liquid dosage form is, for example, described as a pharmaceutical preparation, wherein preferably a bacterial lipase such as *Burkholderia, Pseudomonas* or *Burkholderia plantarii* is used. The application of artificial feeding is also mentioned. However, the teaching according to the invention is not described.

According to Rosenfeld, M. et al.: Nutritional effects of long-term gastrostomy feedings in children with cystic fibrosis; J. Am. Diet. Assoc., 1999, vol., 99, pp. 191-194 nutritional effects of a long-term gastrostomy feeding in children with cystic fibrosis are studied. All patients suffered from pancreatic insufficiency, and pancreatic enzyme supplements were administered to them. The food intake was carried out via a continuous nighttime infusion (see p. 173, left column, 2. paragraph). This procedural method has a number of disadvantages: the patient cannot rest during the night and therefore cannot recover quickly. The pancreatic enzyme supplements were administered before or after the finished food intake during the night or in the morning, which interrupts or prematurely stops the nighttime rest. Additionally, the food is not available in the gastrointestinal tract at the same time as the enzyme supplements. This does not eliminate digestive disorders in the desired manner. Further, the pancreatic enzymes are probably of animal origin, i.e. they come from a pig, so that a risk of contamination with germs is given. Additionally, the known problem is also present that a deficient activity of the pig lipase during the stomach passage is given, as this lipase is active only at a pH value of 5 to 9. Thus, a sufficient effectivity of the enzyme supplements cannot be guaranteed.

US 2010/0239559 A1 describes a food product composition comprising an enzyme selected from the group consisting of lipase, amylase, protease and combinations thereof, wherein the enzyme has been formulated to have an enhanced stability in an aqueous medium, as well as a nutritional supplement. Next to various other possibilities, a bacterial lipase, such as *Pseudomonas cepacia* lipase, is described as well. Additionally, a stomach tube is mentioned as a possible form of administration. In order to be able to provide the enzymes in a stabilized form to enable a continuous stability in an aqueous medium, the enzymes are produced in the form of crystals and, if necessary, are enclosed by polymers. Therefore, other aspects than in the present invention are relevant and other topics are emphasized.

Further, numerous publications are known from prior art which describe the structure of multi-lumen tubes (see for example DE 102 43 208 B4 and U.S. Pat. No. 5,527,280 A).

In some cases, tube feeding may cause problems: for example, diarrhea may occur. This may be because the food was given too fast or was too cold—the tube food should always be at room temperature. Also, an intolerance to a component of the tube food is possible, or the digestion of the patient causes complications. It is therefore appropriate to support digestion in patients with artificial feeding.

In order to improve the digestion in case of artificial feeding, it is for example customary in the enteral nutrition to administer digestive enzymes in the form of solid, enteric-coated, multiparticulate pancreatic enzyme preparations orally or via large-lumen tubes (e.g. 16 to 18 French (=Fr); 1 Fr=0.33 mm outer diameter) boluswise. This is for example described in detail in Shlieout et al. *"Administration of CREON® Pancrelipase Pellets via Gastrostomy Tube is Feasible with No Loss of Gastric Resistance or Lipase Activity"*, Journal of Clinical Investigation, 2011, pp. 1-7. However, this procedure is rather unphysiological and deviates completely from the normal eating habits of healthy people. In addition, no optimal mixing of digestive enzymes with the tube food can be guaranteed, so that the effect is in each case only suboptimal and possibly insufficient and often no significant improvement in digestion results. In addition, in the practical implementation this practice causes additional stress on the patients (e.g. nocturnal wakening).

Disclosure of the Invention: Object, Solution, Advantages

The present invention is therefore based on the object to avoid the known disadvantages of the prior art. In particular, it should be possible to reliably improve the digestion in case of artificial feeding, while additional stress of the patient should be largely avoided.

The described object is solved by the use of a pharmaceutical composition in combination with tube food provided for artificial feeding in the treatment of digestive disorders in case of artificial feeding, wherein the pharmaceutical composition contains or consists of at least one digestive enzyme, preferably a lipase, particularly preferably a bacterial lipase, most preferably burlulipase (INN), in liquid dosage form, wherein the pharmaceutical composition and the tube food are formulated to be administered simultaneously, but separately from each other. Preferably, the pharmaceutical composition and the tube food are formulated in such a way that they can be administered at the same time, without coming in contact with each other in advance. Additionally, it has been found to be advantageous that the pharmaceutical composition and the tube food are formulated in such a way that a continuous administration is possible.

According to a preferred embodiment the invention therefore refers to the use of a pharmaceutical composition with a tube food provided for artificial feeding for producing a combination product in the treatment of digestive disorders in case of artificial feeding, wherein the pharmaceutical composition contains or consists of at least one digestive enzyme, preferably a lipase, particularly preferably a bacterial lipase, most preferably burlulipase (INN) in liquid dosage form, wherein the combination product for administration is formulated in such a way that the pharmaceutical composition and the tube food are formulated to be administered simultaneously, but separately from each other.

The present invention therefore enables the provision for a parallel, continuous administration of a liquid dosage form of a pharmaceutical composition containing at least one digestive enzyme, and of the tube food. By the simultaneous, continuous, but separate administration, an exploitation of the full digestive capacity of the patient is usually achieved.

The term "digestive enzymes" usually refers to enzymes which are preferably derived from the three classes of enzymes required for the digestion of the three basic components of food—lipases for fats, amylases for carbohydrates, proteases for proteins. As such, they are present in healthy persons in sufficient amounts in the exocrine pancreatic secretion.

The current standard of treatment for insufficient digestive capacity based on enzyme deficiency is the administration of preparations containing a porcine pancreatic extract—and thus digestive enzymes from the three aforementioned classes of enzymes. This active ingredient "pancreatin" is monographed in the European Pharmacopoeia (Ph. Eur.) as "pancreatic powder" (pancreas powder), in the US Pharmacopoeia (USP) as "pancreatin" or "pancrelipase".

In the context of the present invention, it is very particularly preferred if the bacterial lipase "burlulipase" (INN) is used as the at least one digestive enzyme contained. As is known, bacteria produce a large number of lipolytically active enzymes. In U.S. Pat. Nos. 5,645,832 or 5,489,530, a lipase extracted from bacteria has already been described in detail. Burlulipase is a triacylglycerol acyl hydrolase (EC 3.1.1.3) which has an amino acid sequence consistent with the lipases produced by *Burkholderia plantarii* and *Burkholderia glumae*. Burlulipase can therefore particularly be produced by a conventional fermentation process using *Burkholderia plantarii*, a non-recombinant Gram-negative bacterium as a production strain.

In particular, burlulipase stands out by its good acid stability in conjunction with a high specific activity, which is largely maintained even at the acidic pH values in the stomach. In contrast, for example, porcine lipase at a pH value in the range of 2.0 to 4.0 after 2 hours already shows an activity which is reduced by 85%. Moreover, burlulipase can be provided advantageously as a liquid formulation, without a loss of activity being observed. It is therefore particularly advantageous that a suitable liquid formulation can be used for artificial feeding and no solid dosage forms, such as multiparticulate forms have to be used.

Pure burlulipase may have a specific activity of more than 3,500 U/mg (tributyrin units per milligram of protein). Due to its high lipolytic activity, burlulipase is particularly suitable for supporting digestive performance in healthy and sick people. The lipase concentration of burlulipase is very high, so that only small amounts of substance, i.e. a lesser mass or volume of solution have to be administered. The pH-specific activity range of burlulipase is between 4 and 9, wherein the molecule is stable in the entire pH-specific activity range and only at pH values below 3 becomes increasingly inactivated already after a short time. Thus burlulipase as an active ingredient overcomes the restrictions regarding the activity and stability of pancreatin from porcine pancreas. The pH-specific activity range of the pancreatic lipase is between 5 and 9, with a marked, acid-related inactivation already below pH 4. This means that by means of burlulipase, a lipolytic action in the gastrointestinal tract can be achieved in many respects much more effectively than with the products for the therapy of maldigestion so far available on the market.

Burlulipase is therefore enzymatically active and stable in a wide pH range as well as storage-stable for several months in a suitable aqueous solution and packaging.

It is preferred that a bacterial lipase in the form of burlulipase is present in the pharmaceutical composition as a digestive enzyme. The pharmaceutical composition containing or consisting of at least one digestive enzyme, preferably a lipase, particularly preferably a bacterial lipase, most preferably burlulipase (INN) in a liquid dosage form, is preferably a liquid dosage form of digestive enzymes. This is, for example, a solution, a suspension or an emulsion. If the above mentioned pharmaceutical composition is a solid or semi-solid dosage form of digestive enzymes, it can be easily converted into such a liquid dosage form by dissolving or dispersing in a physiologically tolerable, usually water-based solvent or dispersing agent.

It has been found to be particularly advantageous if the artificial feeding is carried out with simultaneous administration of the pharmaceutical composition by means of an at least double-lumen tube system, wherein the tube food is administered in one lumen and the pharmaceutical composition in liquid dosage form in the other lumen.

This has the advantage that the pharmaceutical composition does not already come into contact with the tube food beforehand and thus the enzyme(s) already contained are already activated and begin the digestion of the food. By the parallel and continuous administration, the pharmaceutical composition comes into contact with the food only in the stomach or intestine, so that only there the digestion begins and is supported. This makes it possible to significantly improve the digestion of a patient who is fed artificially. Good results were achieved in particular with a correspondingly diluted burlulipase solution.

The parallel and continuous administration of a pharmaceutical composition in the form of a liquid dosage form and tube food is particularly advantageously achieved via an at least double-lumen tube. Lumen refers to the inner cavity of the hose of the tube. The hose of a tube may generally consist of one or more lumens. A gastric tube with only one lumen is thus a simple hose that is constructed like a simple, flexible pipe. A typical example of a gastric tube with only one lumen is a drainage tube that can be used to drain gastric fluid from the stomach to the outside.

A double-lumen tube is therefore a double-barreled tube having two lumens, e.g. a double-barreled gastrointestinal tube, namely a Lagerlof tube, as used for pancreatic function diagnostics for separate suction of gastric secretions and duodenal content. The other properties of the tube system remain unaffected and can be selected accordingly. For example, depending on its length, the tube may end in the stomach (gastric), in the duodenum (duodenal), or in the jejunum (jejunal). Preferably, tubes with more lumens (multi-lumen tubes) may be used, particularly preferred are tubes with 2 or 3 lumens.

The type and material of the tube are not particularly limited. Usually polyvinyl chloride, polyurethane or silicone or silicone rubber is used as a physiologically inert and therefore compatible material for the tube, wherein all tubes are generally designed in such a way that they are radiographically representable. The soft material is oesophagus and mucous membrane friendly. Depending on their use, tubes can have a length of, for example, 100 to 130 cm. The most common sizes are: CH 6 to 8 for newborns, CH 8 to 10 for toddlers, CH 10 to 12 for children, CH 12 to 18 for adults. A Charrière or CH (also Charr or French (=Fr)) in medicine refers to a dimension of the outer circumference of cannulas and catheters/tubes and corresponds to a millimeter of the outer circumference corresponding to about ⅓ mm outer diameter.

The hose used as a tube is therefore only a few millimeters thick, so that the tube food should be absolutely free of larger particles—already clotted protein or crystallizing mineral salts could clog the hose. Thus, a careful maintenance by regular rinsing is required so that the thin tube does not clog.

It is therefore understood that the pharmaceutical composition according to the present invention is provided in such a way that it can be administered through a tube. The criteria that must be met for this purpose are known to the person skilled in the art from prior art.

The use of a pharmaceutical composition containing or consisting of at least one digestive enzyme, preferably a lipase, particularly preferably a bacterial lipase, most preferably burlulipase (INN) in liquid dosage form, in which tube feeding by means of at least a double-lumen tube causes the liquid dosage form containing digestive enzymes and the tube food to be administered separately from each other. The liquid dosage form containing digestive enzymes and the tube food are brought together only in the gastrointestinal system. For this purpose, a tube can be used which is thinner than tubes of the prior art, with which, for example, additionally drugs to improve the digestion are administered to the patient. The additional administration of the pharmaceutical composition in liquid dosage form causes no problems in the use of the tube system: There is no unwanted reflux and no clogging of the tube, since the pharmaceutical composition in its liquid dosage form is suitable for supply by tubes without any problems. Thus, a premature or additional replacement of the tube, caused by reflux or clogging due to drug forms difficult to administer, such as pellets, does not apply.

Another advantage of the invention is that the pharmaceutical composition containing digestive enzymes no longer needs to be added directly to the tube food. Furthermore, it is also not necessary to wake the patient every 3 to 4 hours during the night, for example for an enzyme ingestion. Rather, the pharmaceutical composition containing digestive enzymes can be administered in its liquid dosage form parallel to the tube food, so that the patient can sleep through the night despite artificial feeding. As a result, the patient is significantly less stressed and can recover faster. Even in the case of unconscious or comatose and ventilated patients, this represents a significant relief for both the patient and the nursing staff.

According to a preferred embodiment of the invention, the pharmaceutical composition containing or consisting of at least one digestive enzyme, preferably a lipase, particularly preferably a bacterial lipase, most preferably Burlulipase (INN) in a liquid dosage form and the tube food are each supplied from a separate container to the respective lumen of the at least double-lumen tube system. Alternatively, the pharmaceutical composition containing or consisting of at least one digestive enzyme, preferably a lipase, particularly preferably a bacterial lipase, most preferably burlulipase (INN) in a liquid dosage form and the tube food may also be provided in a multi-compartment container in separate compartments and may be provided through separate feed lines to the respective lumen of the at least double-lumen tube system Advantageously, the rate (volume per time) of administration of the pharmaceutical composition and the tube food is then individually controllable by separate, individually controllable infusion or pumping systems for each lumen of the at least double-lumen tube system.

In using the pharmaceutical composition containing digestive enzymes, it is advantageous that the patients, according to a preferred embodiment, may be fed physiologically more tolerably under parallel, continuous administration of digestive enzymes and with optimal utilization of the potential of the medication. This type of additional administration of digestion assisting medicine is very similar to the normal diet and therefore less stressful for the patient.

The use of an at least two-lumen tube causes the tube food to come into contact with the digestive enzyme(s) only after exiting the lumen. Thus, an unwanted pre-digestion of the food can be excluded. Furthermore, the use of the pharmaceutical composition containing digestive enzymes also allows administration through a nasogastric tube. This has the advantage that a tube with a narrow lumen can be used, since the pharmaceutical composition containing digestive enzymes is in liquid dosage form, most preferably in the form of a burlulipase solution.

Preferably, the tube system is in the form of a tube which ends in the stomach, duodenum or jejunum. Furthermore, it is preferred that the tube system is in the form of a tube which is a nasogastric tube, nasointestinal tube, nasoduodenal tube, nasojejunal tube, PEJ tube or a PEG tube, and/or that the tube system is designed with two or more lumens.

In the practical implementation of the present invention, therefore, the usual additional stress of the patients, i.e. wakening to administer the medicine assisting the digestion during the night, can be avoided. Administration of the pharmaceutical composition assisting the digestion is always co-administered with the tube food, as a result of which the patient does not need to be additionally bothered for the administration of the medication.

Furthermore, it has been found that the use of a bacterial lipase, in particular burlulipase, as the at least one digestive enzyme contained in the pharmaceutical composition offers particular advantages in the present invention. Thus, the additional administration of bacterial lipase, in particular burlulipase, significantly increases the proportion of lipases and thus significantly increases fat digestion. The fat digestion usually is of particular relevance for patients with digestive weakness. Overall, this leads to a better tolerability of the food in the patient.

The bacterial lipase used, preferably burlulipase, is preferably not chemically modified, so that a natural product is used which has not undergone further chemical modifications or treatments. In addition, the bacterial lipase is a product which does not originate from animals, so that the risk of possible diseases due to animal sources, such as viral diseases, is generally excluded.

Another advantage is that the administration of burlulipase appears to be a well-tolerated therapeutic option with low-side-effects.

In addition, the pH value of the stomach or intestine is not altered by a bacterial lipase, in particular burlulipase, so that likewise no unwanted side effects are caused in the patient and no additional medicaments for controlling or adjusting the pH value of the gastrointestinal region must be taken.

The pharmaceutical composition containing digestive enzymes is administered in liquid dosage form, resulting in an easy handling by the nursing staff and in an effective administration to the patient. A liquid dosage form offers the possibility of a convenient and exact dosage with optimal conditions for a homogeneous distribution of the digestive enzyme(s) contained in the (tube) food in the stomach.

The liquid dosage form can be, for example, solutions, suspensions or emulsions. A suspension refers to a two-phase system consisting of solid inner phase, e.g. the undissolved active ingredient burlulipase, which is dispersed in a liquid.

Liquid administration forms can be prepared either by directly formulating the at least one digestive enzyme contained in the pharmaceutical composition as a liquid dosage form and then, if appropriate, diluting it to a stage appropriate for use, by dissolving the pharmaceutical composition containing digestive enzymes in an aqueous or nonaqueous solvent or by suspending or emulsifying the pharmaceutical composition containing digestive enzymes in a suitable dispersion medium. As a liquid dosage form for the at least one digestive enzyme contained in the pharmaceutical composition, preferably a lipase, particularly preferably a bacterial lipase, most preferably burlulipase (INN), basically any known liquid dosage form is suitable. Examples include solutions, including infusion solutions and injection solutions, suspensions, emulsions, oils, juices, syrups, tinctures, drops, water, aromatic waters, aqueous acids, teas and the like.

In particular, liquid dosage forms, such as solutions, suspensions and emulsions, are advantageous, since their concentration can still be adjusted exactly and suitably as needed by simple dilution and then allows a finely graduated dosage—if necessary, even individual drops could be administered.

Burlulipase may preferably be present in the liquid dosage form at a concentration of 0.0002 mg/ml to 50 mg/ml based on burlulipase protein.

The pharmaceutical composition containing or consisting of at least one digestive enzyme, preferably a lipase, particularly preferably a bacterial lipase, most preferably burlulipase (INN) in a liquid dosage form, may have one or more solvents and/or one or more excipients. The solvents and/or excipients are then preferably selected from
water
salts
organic acids
amino acids
detergents
sugars
oils
viscosity regulators.

Surprisingly, it is sufficient if the pharmaceutical composition has only one digestive enzyme, in the present case a lipase, in particular burlulipase, in order to effectively medicate corresponding indigestion. Other enzymes, such as proteases or amylases, not necessarily have to be present.

The additional administration of a lipase, in particular burlulipase, as part of an artificial feeding increases the amount of lipases available for the fat digestion, which is usually crucial for people with digestive problems. The present invention thus achieves an optimization of the digestive power (fat digestion and absorption) in an artificial feeding by increasing the total lipase activity.

The efficacy of bacterial lipase treatment in the form of burlulipase has already been demonstrated in patients with digestive problems, such as patients suffering from exocrine pancreatic insufficiency due to mucoviscidosis. By this, the digestion has been significantly improved, a significant reduction of otherwise occurring fat diarrhea has also been observed.

BRIEF DESCRIPTION OF THE DRAWINGS

Hereinafter, the present invention will be explained in detail with reference to figures. However, the invention should not be limited thereto. The drawings show the following.

PREFERRED EMBODIMENTS OF THE INVENTION

Figure 1:
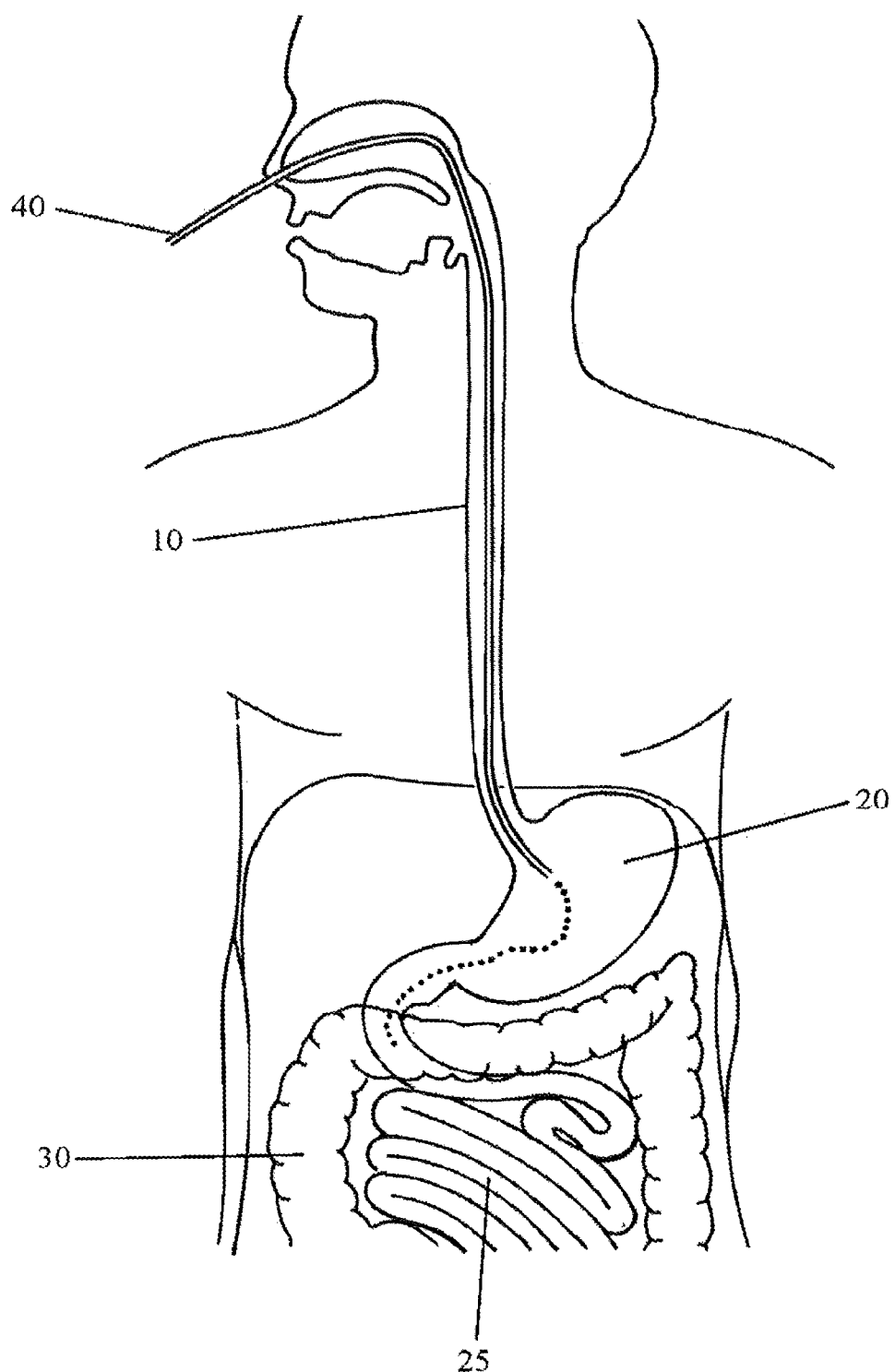
FIG. 1 an exemplary tube system in the form of a nasogastric or nasointestinal tube in the human body using a schematic representation.

FIG. 1 shows an exemplary embodiment for a tube system in the form of a nasogastric or nasogastric tube in a schematic view, illustrated in a cross section of the human body.

The procedure for the use is as follows: First, a pharmaceutical composition containing or consisting of at least one digestive enzyme, preferably a lipase, particularly preferably a bacterial lipase, most preferably burlulipase (INN) in liquid dosage form, is prepared. This can for example be done in advance industrially, but also in a hospital or clinic where the patient is located. For this purpose, a storage-stable dosage form for example containing a bacterial lipase, is provided, which is available in solid, semi-solid or already liquid form or may already be present. Most preferably, a concentrated burlulipase solution is used. Unless it itself already meets the appropriate criteria, this dosage form is then transferred, in particular by dissolution, dispersion and/or dilution, into a suitably diluted liquid dosage form suitable for administration by a tube, for example by using water. A generally suitable liquid dosage form for this purpose is, for example, a suspension, emulsion or solution.

Furthermore, a tube food suitable and intended for artificial feeding is provided. This is tailored to the respective patient, depending on age, height and weight, health and so on. For use, the pharmaceutical composition is then formulated in combination with the tube food for an administration which is simultaneous but separate from each other. Both the tube food and the pharmaceutical composition are therefore simultaneously available, but they are not in direct contact with each other, but are present separate from each other. Both components are thus provided in combination, separately, but are administered simultaneously and come in contact with each other only after the ingestion by the patient, to effect the digestion in the gastrointestinal tract.

This liquid dosage form and the tube food are then administered to the patient via a tube system. This is carried out in particular continuously and/or preferably via a multi-lumen tube. FIG. 1 shows how such a nasogastric or nasointestinal tube 40 is present in the human digestive system, which, depending on the length of the tube 40, ends in the stomach 20 or in the small intestine 25 (shown in dashed lines in FIG. 1). In the example shown, the tube should represent a double-lumen tube 40. However, multi-lumen tubes other than those shown can also be used.

The liquid dosage form containing at least one digestive enzyme, preferably a lipase, particularly preferably a bacterial lipase, most preferably Burlulipase (INN), is supplied through one of the lumens of the double-lumen tube 40, while the tube food is applied in parallel through the other lumen. At the tube mouth, the liquid dosage form of the present invention and the tube food simultaneously flow directly and evenly from the two lumens into the stomach or the duodenum and thus provide optimal conditions for a homogeneous mixing.

The end of the tube 40 may be in the stomach 20 or in the duodenum, i.e. in the first portion of the small intestine 25, with the location in the duodenum often being more advantageous. According to a preferred embodiment, the liquid dosage form and the tube food can each be supplied from a separate container to the respective channel of the double-lumen tube 40, but also from a multi-compartment container with a corresponding feed line to the tube 40. The rate (volume per time) of the application is advantageously individually controllable for each channel by separate, separately controllable infusion or pump systems.

Figure 2:
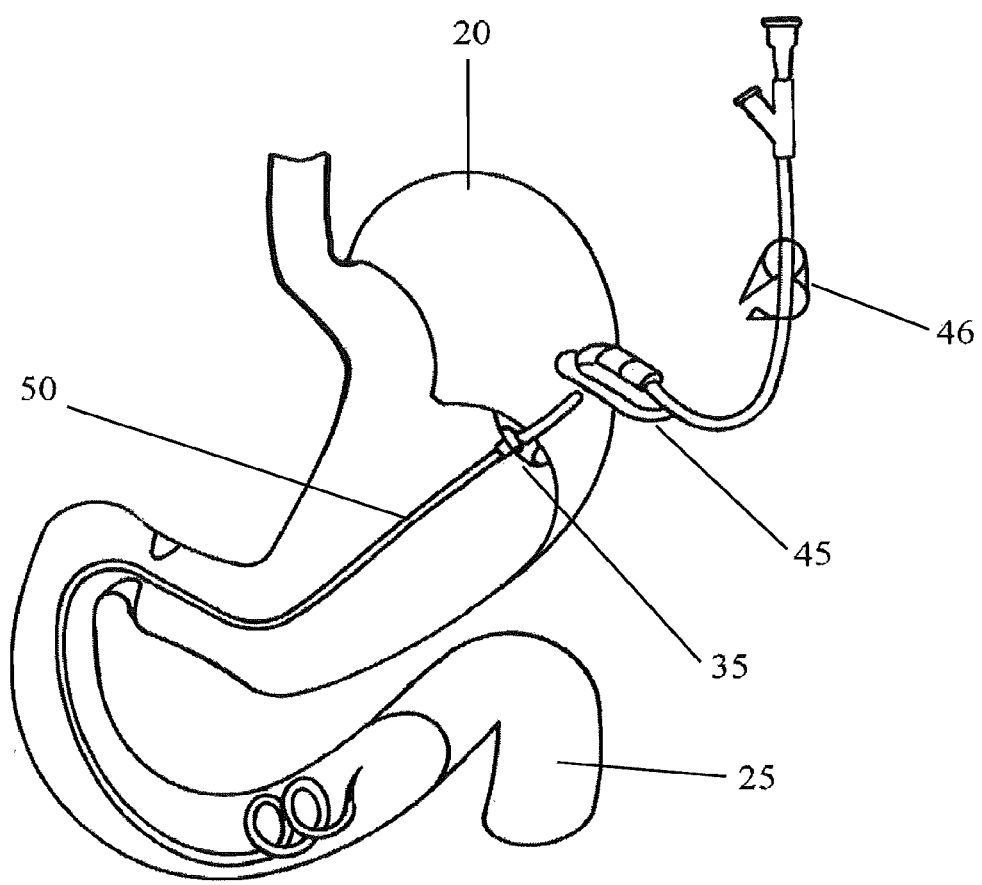
FIG. 2 another exemplary tube system in the form of a PEG or PEJ tube in the human body using a schematic representation, FIG. 3 an exemplary two-lumen tube in a schematic side view and FIGS. 4*a* 4*b* and 4*c* a sectional view through the tube along the line 3-3 of FIG. 3 in enlargened views

FIG. 2 shows a further exemplary tube system in the form of a PEG or PEJ tube using a schematic view. Under endoscopic control, the feeding tube is placed directly in the stomach (PEG) or in the upper small intestine (PEJ). FIG. 2 shows a schematic section of the gastrointestinal system with such a tube 50. In the example shown, the double-lumen tube 50 is fixed to the inner wall of the stomach 20 by an inner silicone retaining plate 35. In addition, the tube 50 is secured to the abdominal wall by an outer retaining plate 45 and a hose clamp 46. Also in the PEJ tube 50 shown, the liquid dosage form containing at least one digestive enzyme, preferably a lipase, particularly preferably a bacterial lipase, most preferably Burlulipase (INN), is applied through one of the lumens of the tube while simultaneously the patient is fed the tube food separately through another lumen.

Figure 3:
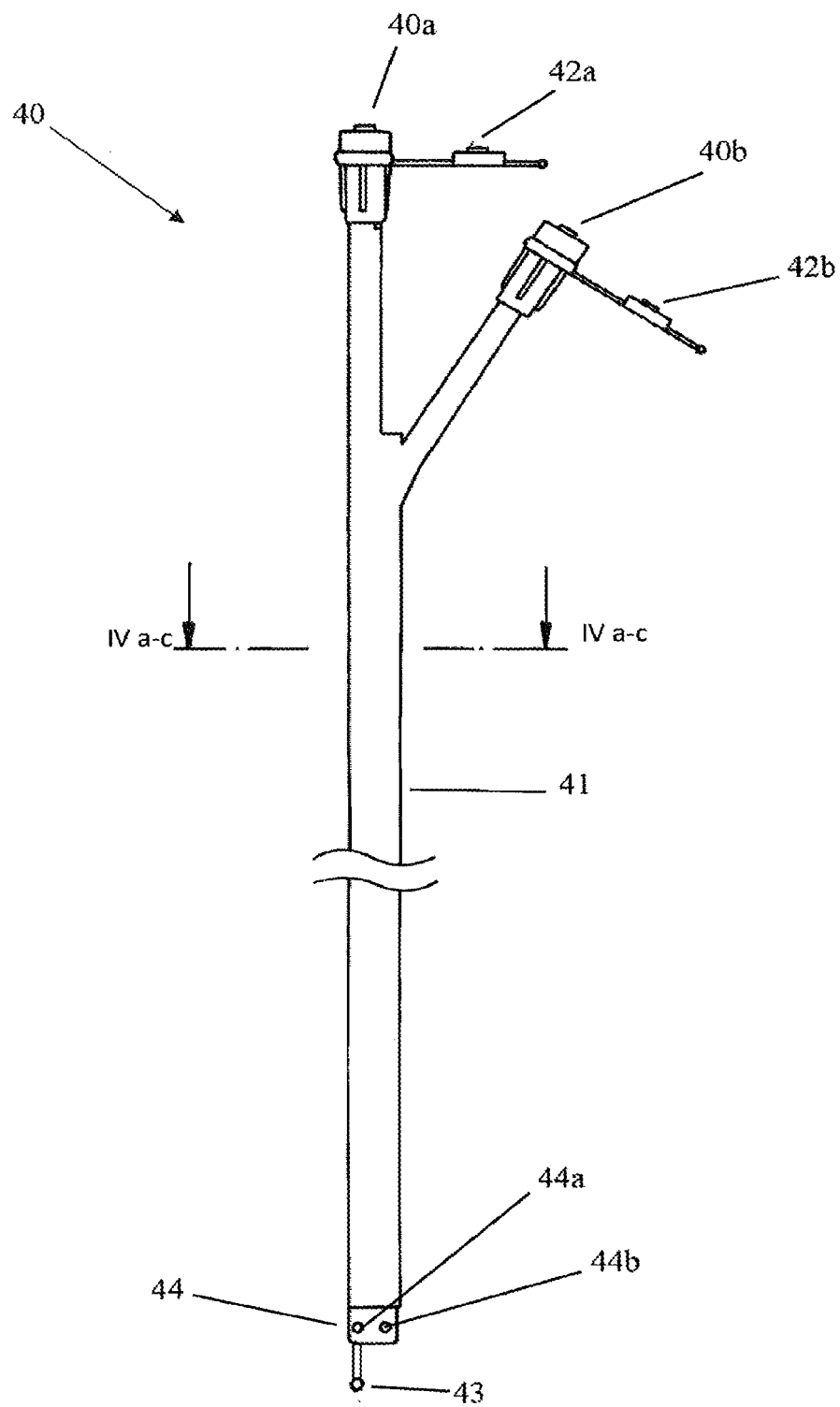
Figure 4:
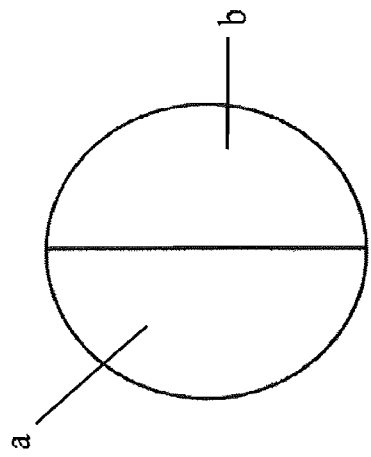
Figure 4:
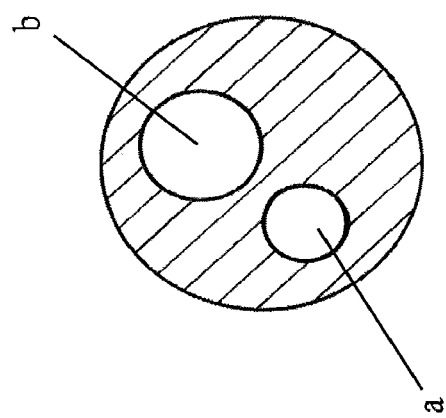
Figure 4:
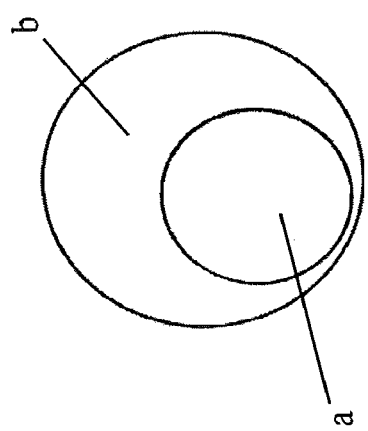

In FIG. 3, an exemplary two-lumen tube 40 is shown in a schematic view. The tube 40 has a flexible tube hose 41 made of polyurethane with a length of 100 cm, in order to be inserted into the duodenum, or the jejunum of the patient. The tube 40 is a double-lumen tube and has two lumens a and b. The first lumen a can have an inner diameter which is identical to or different from that of the second lumen b. This is shown, for example, in FIGS. 4a, 4b and 4c, which show a sectional view through the tube along the line 3-3 of FIG. 3 in an enlargened scale.

In FIG. 3, the tube 40 at the distal end has an olive 44, which may be provided with a handle extension 43, in order to grip it, for example, with an endoscope. The olive 44 has apertures 44a and 44b distributed in the side wall, some of which are arranged in the area of the first lumen a and some in the area of the second lumen b, so that liquid from the first lumen a may exit through the associated openings 44a, and liquid from the second lumen b may exit through the associated openings 44b.

At the proximal end of the tube hose 41, a connecting piece is attached, in the example shown, a positive luer-lock connecting piece 40a with a cap 42a, which is connected to the first lumen a. The second lumen b is connected to the other connecting piece 40b and is also provided with a cap 42b. Other embodiments are also possible.

For example, with the tube the liquid pharmaceutical composition can be administered through the first lumen a, and the tube food through the second lumen b. Therefore, both liquids are mixed only after exiting the tube 40 through the openings 44a and 44b, without being previously in contact with each other.

It is therefore understandable that patients who must be fed artificially, by the additional simultaneous administration of the pharmaceutical composition, preferably containing burlulipase, in liquid dosage form, advantageously will have a significantly better digestion. As a result, additional complications from digestive problems, such as diarrhea, can be avoided in patients.

LIST OF REFERENCE NUMBERS 10 esophagus
20 stomach
25 small intestine
30 large intestine
35 silicone retaining plate
40 double-lumen tube
41 tube hose
40a,b connecting piece
42a,b cap
43 handle extension
44 olive
44a,b openings
a first lumen
b second lumen
45 outer retaining plate
45 hose clamp
50 double-lumen PEG tube

The invention claimed is:

1. A method for the treatment of a digestive disorder, comprising administering to a subject in need thereof a pharmaceutical composition in combination with a tube food provided for artificial feeding, wherein the pharmaceutical composition is in liquid dosage form and comprises at least one digestive enzyme, and wherein the pharmaceutical composition and the tube food are administered simultaneously, but separately from each other.

2. The method of claim 1, wherein the at least one digestive enzyme is a lipase.

3. The method of claim 1, wherein the at least one digestive enzyme is a bacterial lipase.

4. The method of claim 1, wherein the pharmaceutical composition and the tube food are formulated to be administered simultaneously, but separately from each other in such a way that they can be supplied by an at least double-lumen tube system, wherein the tube food is supplied to one lumen of the tube system and the pharmaceutical composition in liquid dosage form is supplied to another lumen of the tube system.

5. The method of claim 1, wherein the liquid dosage form is a solution, a suspension or an emulsion.

6. The method of claim 1, wherein the tube food is supplied by a tube system, wherein the tube system is selected to be in the form of a tube which ends in the stomach, in the duodenum or in the jejunum.

7. The method of claim 1, wherein the tube food is supplied by a tube system, wherein:
  (a) the tube system is selected from the group consisting of a nasogastric tube, nasointestinal tube, nasoduodenal tube, nasojejunal tube, PEJ tube and a PEG tube, or
  (b) the tube system is a tube system having two or more lumens; or
  both (a) and (b).

8. The method of claim 4, wherein the pharmaceutical composition and the tube food are each supplied from a separate container to the respective lumen of the at least double-lumen tube system.

9. The method of claim 4, wherein the pharmaceutical composition and the tube food are provided in a multi-compartment container in separate compartments and are supplied through separate feed lines to the respective lumen of the at least double-lumen tube system.

10. The method of claim 4, wherein rates (volume per time) of administration of the pharmaceutical composition and the tube food are individually controllable by separate, individually controllable infusion or pumping systems for each lumen of the at least two-lumen tube system.

11. The method of claim 1, wherein the pharmaceutical composition further comprises one or more solvents and/or one or more excipients.

12. The method of claim 3, wherein the bacterial lipase is present in the form of burlulipase (INN).

13. The method of claim 12, wherein the burlulipase (INN) is present, in the pharmaceutical composition in liquid dosage form in a concentration of 0.0002 mg/ml to 50 mg/ml based on the burlulipase protein.

14. The method of claim 11, wherein the pharmaceutical composition comprises water as the one or more solvents.

* * * * *